(12) United States Patent
Hossainy et al.

(10) Patent No.: US 6,986,899 B2
(45) Date of Patent: Jan. 17, 2006

(54) COMPOSITION FOR COATING AN IMPLANTABLE PROSTHESIS

(75) Inventors: Syed F. A. Hossainy, Fremont, CA (US); Debbie Sanders-Millare, San Jose, CA (US); Steven Z. Wu, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 87 days.

(21) Appl. No.: 10/639,984

(22) Filed: Aug. 12, 2003

(65) Prior Publication Data

US 2004/0047978 A1 Mar. 11, 2004

Related U.S. Application Data

(62) Division of application No. 10/180,359, filed on Jun. 25, 2002, now Pat. No. 6,733,768, which is a division of application No. 09/633,081, filed on Aug. 4, 2000, now Pat. No. 6,451,373.

(51) Int. Cl.
*A61F 2/02* (2006.01)
*B32B 9/00* (2006.01)
*B32B 27/00* (2006.01)
*D02G 3/00* (2006.01)

(52) U.S. Cl. .................. 424/423; 428/392; 428/394
(58) Field of Classification Search .............. 424/423; 428/392, 394
See application file for complete search history.

(56) References Cited

U.S. PATENT DOCUMENTS

| 4,329,383 | A | | 5/1982 | Joh ........................ 428/36 |
| 4,351,337 | A | * | 9/1982 | Sidman .................... 424/425 |
| 4,733,665 | A | | 3/1988 | Palmaz ..................... 128/343 |
| 4,800,882 | A | | 1/1989 | Gianturco ................. 128/343 |
| 4,882,168 | A | | 11/1989 | Casey et al. .............. 424/468 |
| 4,886,062 | A | | 12/1989 | Wiktor .................... 128/343 |
| 4,941,870 | A | | 7/1990 | Okada et al. ............... 600/36 |

(Continued)

FOREIGN PATENT DOCUMENTS

| EP | 0 301 856 | 2/1989 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |

(Continued)

OTHER PUBLICATIONS

Anonymous, *Cardiologists Draw—Up The Dream Stent*, Clinica 710:15 (Jun. 17, 1996), http://www.dialogweb.com/cqi/document?req+1061848202959, printed Aug. 25, 2003 (2 pages).

(Continued)

*Primary Examiner*—Carlos A. Azpuru
(74) *Attorney, Agent, or Firm*—Squire, Sanders & Dempsey L.L.P.

(57) ABSTRACT

A composition for coating an implantable prosthesis, such as a stent is disclosed. A method of forming the composition is also disclosed.

36 Claims, 1 Drawing Sheet

U.S. PATENT DOCUMENTS

| | | | |
|---|---|---|---|
| 4,977,901 A | 12/1990 | Ofstead | 128/772 |
| 5,112,457 A | 5/1992 | Marchant | 204/165 |
| 5,165,919 A | 11/1992 | Sasaki et al. | 424/488 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,527,337 A | 6/1996 | Stack et al. | 606/198 |
| 5,569,463 A | 10/1996 | Helmus et al. | 424/426 |
| 5,578,073 A | 11/1996 | Haimovich et al. | 623/1 |
| 5,605,696 A | 2/1997 | Eury et al. | 424/423 |
| 5,609,629 A | 3/1997 | Lindegren | 623/1 |
| 5,624,411 A | 4/1997 | Tuch | 604/265 |
| 5,628,730 A | 5/1997 | Shapland et al. | 604/21 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,713,949 A | 2/1998 | Jayaraman | 623/1 |
| 5,716,981 A | 2/1998 | Hunter et al. | 514/449 |
| 5,735,897 A | 4/1998 | Buirge | 623/12 |
| 5,746,998 A | 5/1998 | Torchilin et al. | 424/9.4 |
| 5,766,710 A | 6/1998 | Turnlund et al. | 428/36.1 |
| 5,769,883 A | 6/1998 | Buscemi et al. | 623/1 |
| 5,776,184 A | 7/1998 | Tuch | 623/1 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,843,172 A | 12/1998 | Yan | 623/1 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,925,720 A | 7/1999 | Kataoka et al. | 525/523 |
| 5,955,509 A | 9/1999 | Webber et al. | 514/772.7 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |
| 6,033,582 A | 3/2000 | Lee et al. | 216/37 |
| 6,042,875 A | 3/2000 | Ding et al. | 427/2.24 |
| 6,051,276 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,203,551 B1 | 3/2001 | Wu | 606/108 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,494,862 B1 | 12/2002 | Ray et al. | 604/96.01 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,527,801 B1 | 3/2003 | Dutta | 623/1.46 |
| 6,527,863 B1 | 3/2003 | Pacetti et al. | 118/500 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,656,506 B1 * | 12/2003 | Wu et al. | 424/489 |
| 6,673,385 B1 * | 1/2004 | Ding et al. | 427/2.28 |
| 2001/0018469 A1 | 8/2001 | Chen et al. | 523/121 |
| 2001/0037145 A1 | 11/2001 | Guruwaiya et al. | 623/1.15 |
| 2002/0077693 A1 | 6/2002 | Barclay et al. | 623/1.13 |
| 2002/0091433 A1 | 7/2002 | Ding et al. | 623/1.2 |
| 2002/0155212 A1 | 10/2002 | Hossainy | 427/2.25 |
| 2003/0065377 A1 | 4/2003 | Davila et al. | 623/1.13 |
| 2003/0099712 A1 | 5/2003 | Jayaraman | 424/486 |
| 2004/0052859 A1 * | 3/2004 | Wu et al. | 424/490 |

FOREIGN PATENT DOCUMENTS

| | | |
|---|---|---|
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |

| | | |
|---|---|---|
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/23228 | 6/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/026162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin–coated stents cut complications by 30%a*; Clinica 732:17 (Nov. 18, 1996), http://www.dialogweb.com/cqi/document?req+1061847871753, printed Aug. 25, 2003 (2 pages).

Anonymous, *Rolling Therapeutic Agent Loading Device for Therapeutic Agent Delivery or Coated Stent* ( Abstract 434009), Res. Disclos. pp. 974–975 (Jun. 2000).

Anonymous, *Stenting continues to dominate cardiology*, Clinica 720:22 (Sep. 2, 1996), http://www.dialogweb.com/cqi/document?req+1061848017752, printed Aug. 25, 2003 (2 pages).

Aoyagi et al., *Preparation of cross–linked aliphatic polyester and application to thermo–responsive material*, Journal of Controlled Release 32:87–96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259–1274 (Oct. 1991).

Chung et al., *Inner core segment design for drug delivery control of thermo–responsive polymeric micelles*, Journal of Controlled Release 65:93–103 (2000).

Dev et al., *Kinetics of Drug Delivery to the Arterial Wall Via Polyurethane–Coated Removable Nitinol Stent: Comparative Study of Two Drugs*, Catheterization and Cardiovascular Diagnosis 34:272–278 (1995).

Dichek et al., *Seeding of Intravascular Stents with Genetically Engineered Endothelial Cells*, Circ. 80(5):1347–1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701–1), Abstract (Feb. 1994).

Helmus, *Overview of Biomedical Materials*, MRS Bulletin, pp. 33–38 (Sep. 1991).

Herdeg et al., *Antiproliferative Stent Coatings: Taxol and Related Compounds*, Semin. Intervent. Cardiol. 3:197–199 (1998).

Inoue et al., *An AB block copolymer of oligo(methyl methacrylate) and poly(acrylic acid) for micellar delivery of hydrophobic drugs*, Journal of Controlled Release 51:221–229 (1998).

Kataoka et al., *Block copolymer micelles as vehicles for drug delivery*, Journal of Controlled Release 24:119–132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259–268 (1994).

Liu et al., *Drug release characteristics of unimolecular polymeric micelles*, Journal of Controlled Release 68:167–174 (2000).

Marconi et al., *Covalent bonding of heparin to a vinyl copolymer for biomedical application*, Biomaterial 18(12):885–890 (1997).

Matsumaru et al., *Embolic Materials For Endovascular Treatment of Cerebral Lesions*, J. Biomater. Sci. Polymer Edn 8(7):555–569 (1997).

Miyazaki et al., *Antitumor Effect of Implanted Ethylene–Vinyl Alcohol Copolymer Matrices Containing Anticancer Agents on Ehrlich Ascites Carcinoma and P388 Leukemia in Mice*, Chem. Pharm. Bull. 33(6) 2490–2498 (1985).

Miyazawa et al., *Effects of Pemirolast and Tranilast on Intimal Thickening After Arterial Injury in the Rat*, J. Cardiovasc. Pharmacol., pp. 157–162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pernirolast Potassium, on Restenosis After Percutaneous Transluminal Coronary Angioplasty*, American Heart Journal 136(6):1081–1087 (Dec. 1998).

Ozaki et al., *New Stent Technologies*, Progress in Cardiovascular Diseases, vol. XXXIX(2):129–140 (Sep./Oct. 1996).

Pechar et al., *Poly(ethylene glycol) Multiblock Copolymer as a Carrier of Anti–Cancer Drug Doxorubicin*, Bioconjucate Chemistry 11(2):131–139 (Mar./Apr. 2000).

Peng et al., *Role of polymers in improving the results of stenting in coronary arteries*, Biomaterials 17:685–694 (1996).

Shigeno, *Prevention of Cerebrovascular Spasm By Bosetan, Novel Endothelin Receptor*; Chemical Abstract 125:212307 (1996).

van Beusekom et al., *Coronary stent coatings*, Coronary Artery Disease 5(7):590–596 (Jul. 1994).

Wilensky et al., *Methods and Devices for Local Drug Delivery in Coronary and Peripheral Arteries*, Trends Cardiovasc. Med. 3(5):163–170 (1993).

Yokoyama et al., *Characterization of physical entrapment and chemical conjugation of adriamycin in polymeric micelles and their design for in vivo delivery to a solid tumor*, Journal of Controlled Release 50:79–92 (1998).

* cited by examiner

US 6,986,899 B2

COMPOSITION FOR COATING AN IMPLANTABLE PROSTHESIS

CROSS REFERENCE

This is a division of U.S. patent application Ser. No. 10/180,359 filed Jun. 25, 2002, now U.S. Pat. No. 6,733,768 which is a division of Ser. No. 09/633,081, filed Aug. 4, 2000, now U.S. Pat. No. 6,451,373.

BACKGROUND OF THE INVENTION

1. Field of the Invention

The present invention relates generally to implantable devices, examples of which include stents and grafts. More particularly, the present invention is directed to an improved method of coating an implantable device with a therapeutic substance.

2. Description of the Related Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced though the coronary vasculature until the balloon portion is positioned across the occlusive lesion. Once in position across the lesion, the balloon is inflated to a predetermined size to radially press against the atherosclerotic plaque of the lesion to remodel the vessel wall. The balloon is then deflated to a smaller profile to allow the catheter to be withdrawn from the patient's vasculature.

A problem associated with the above procedure includes formation of intimal flaps or torn arterial linings which can collapse and occlude the vessel after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a prosthesis, examples of which include stents and grafts, is implanted.

Stents are scaffoldings, usually cylindrical or tubular in shape, which function to physically hold open and, if desired, to expand the wall of the vessel. Typically stents are capable of being compressed, so that they may be inserted through small cavities via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Synthetic vascular grafts are vessel-like configurations that may be positioned into the host blood vessel as a replacement for a diseased or occluded segment that has been removed. Alternatively, a graft may be sutured to the host vessel at each end so as to form a bypass conduit around a diseased or occluded segment of the host vessel.

Although stents and grafts are significant innovations in the treatment of occluded vessels, there remains a need for administering therapeutic substances to the treatment site. To provide an efficacious concentration to the treatment site, systemic administration of the therapeutic substance often produces adverse or toxic side effects for the patient. Local delivery is a highly suitable method of treatment, in that smaller levels of therapeutic substances, as compared to systemic dosages, are concentrated at a specific site. Local delivery produces fewer side effects and achieves more effective results.

One technique for the local delivery of therapeutic substances is through the use of medicated coatings on implantable devices. A common method for medicating a prosthesis involves the use of a polymeric carrier coated onto the surface of the prosthesis. A composition is formed by dissolving a therapeutic substance in a solution containing a polymer and a solvent. The composition is applied to the prosthesis using conventional techniques, such as spray-coating or dip-coating. The solvent is then removed, leaving on the prosthesis surface a coating of the polymer and the therapeutic substance impregnated in the polymer.

A shortcoming of the above-described method is the burst effect, in which an initial rapid release of therapeutic substance upon implantation of the prosthesis is followed by a slower, sustained release of therapeutic substance. Of the various factors which contribute to the burst effect, two factors stem from drying a solution-based coating. First, solution-based coating almost invariably results in an asymmetric distribution of therapeutic substance in the matrix. A higher concentration of therapeutic substance exists at the drying surface, or polymer-air interface, since the therapeutic substance concentrates where the solvent was at the end of the drying process. Additionally, a solvent-dried system may result in the therapeutic substance being in an amorphous phase. When the therapeutic substance is amorphous, as opposed to crystalline, the therapeutic substance exists as individual molecules in the matrix. These molecules may diffuse freely without first having to dissolve into the matrix as they would from a more crystalline phase and therefore contribute to the initial burst of therapeutic substance upon implantation of the prosthesis.

Another shortcoming of the above-described method for medicating a prosthesis is that the method does not facilitate processing every therapeutic substance with every polymer and solvent combination. Some therapeutic substances are very delicate and thus cannot tolerate processing in the presence of a solvent and or a polymer for extended periods of time. This is especially true for peptide-type therapeutic substances, such as actinomycin D and others, having tertiary structure susceptible to transmutation from their native forms.

SUMMARY OF THE INVENTION

A method of producing a composition which can be used to coat an implantable medical device is provided, comprising combining a therapeutic substance and a fluid, wherein the therapeutic substance has a limited solubility in the fluid such that the fluid is not capable of significantly dissolving the therapeutic substance wherein a majority amount of the therapeutic substance is suspended in particle or solid form in the fluid and is not in dissolution with the fluid and wherein the composition can be applied to an implantable medical device that can retain the therapeutic substance, for the local delivery of the substance, upon removal of the fluid. The device can be a balloon-expandable stent, a self-expandable stent, or a graft. In one embodiment, greater than 50% and less than or equal to 100% of the therapeutic substance is suspended as particles or is in solid form in the composition. In another embodiment, 70% to about 100% of the therapeutic substance is suspended as particles or is in solid form in the composition. The particles of the therapeutic substance can have diameters ranging from about 0.5 microns to about 20 microns. The composition can additionally include a suspension stabilizer to reduce the flocculation of the therapeutic substance within the composition.

The fluid can be a combination of at least two fluids. In one embodiment, at least one of the fluids is a solvent for the therapeutic substance and at least one of the fluids is a non-solvent for the therapeutic substance.

The method can also include adding a polymeric material to the composition. The fluid can be capable of dissolving the polymeric material.

DETAILED DESCRIPTION OF THE EMBODIMENTS

Prosthesis

Figure 1:
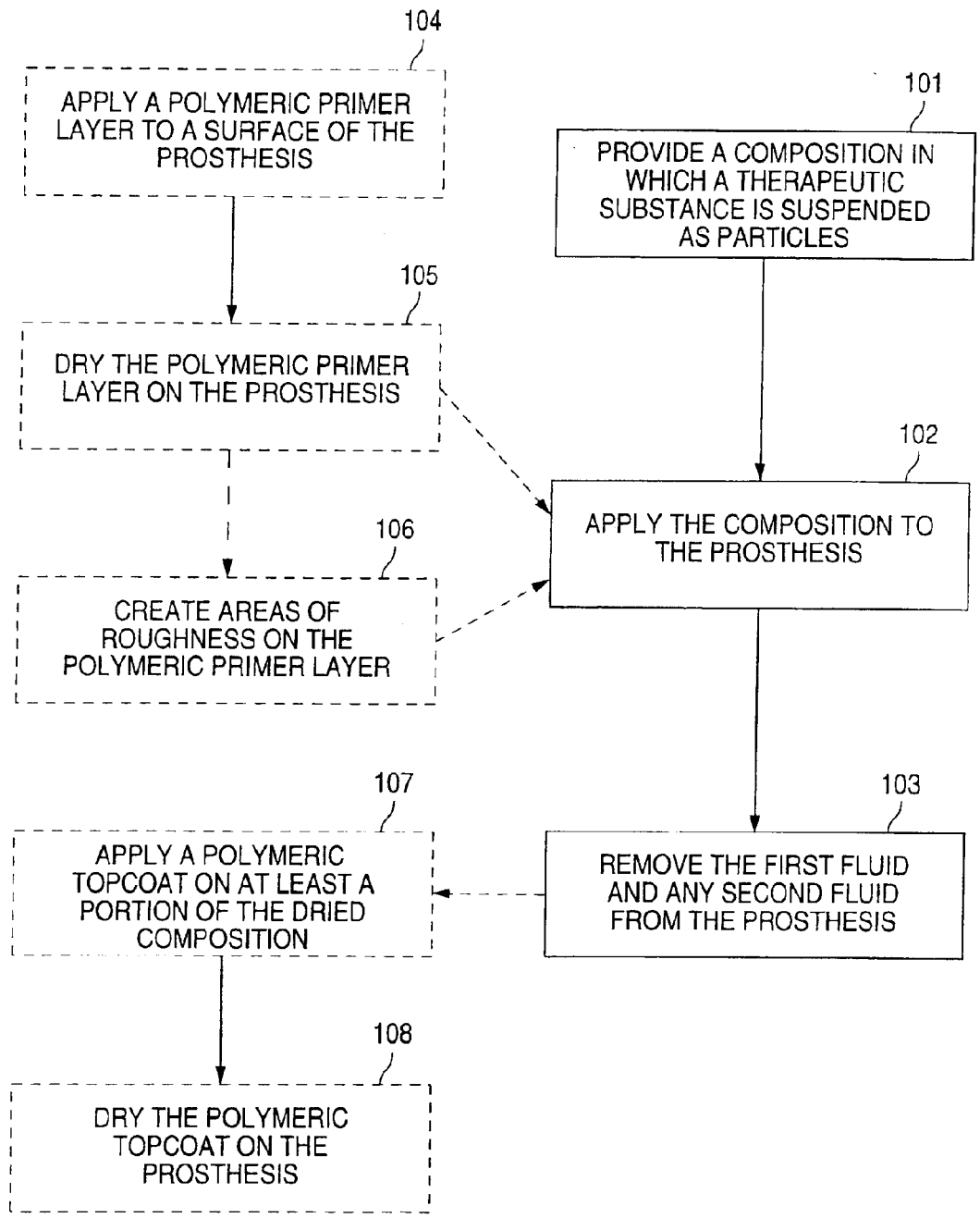
FIG. 1 is a flowchart illustrating a method of forming a coating onto a surface of a prosthesis in accordance with the various disclosed embodiments.

The prosthesis used in conjunction with the present invention may be any implantable device, examples of which include self-expandable stents, balloon-expandable stents, and grafts, among other possibilities. The underlying structure of the prosthesis can be virtually any design. The prosthesis can be made of a metallic material or an alloy such as, but not limited to, stainless steel, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The prosthesis may also be made from bioabsorbable or biostable polymers. A polymeric prosthesis should be compatible with the composition.

Preparation of the Composition

FIG. 1 illustrates a method 100 of forming a coating onto a surface of the above-described prosthesis. The coating of the present invention is formed from a selected composition in which a therapeutic substance is suspended as particles. In act 101 of method 100, such a composition is provided as described below.

In accordance with some embodiments, a predetermined amount of a therapeutic substance is added to a predetermined amount of a first fluid. Of the total amount of therapeutic substance added to the first fluid, from about 70% to 100%, or more particularly from about 95% to 100%, of the therapeutic substance should be suspended as particles in the first fluid and from 0% to about 30%, or more particularly from 0% to about 5% of the therapeutic substance may be in solution with the first fluid. Thus, the therapeutic substance has a limited solubility of no more than 30% in the first fluid. When the prosthesis upon which the coating is to be formed is a stent, the size of the suspended particles of therapeutic substance can range from about 0.5 microns in diameter to about 2 microns in diameter. When the prosthesis upon which the coating is to be formed is a vascular graft, the size of the suspended particles of therapeutic substance can range from about 0.5 microns in diameter to about 20 microns in diameter, or more particularly from about 8 microns in diameter to about 13 microns in diameter. The therapeutic substance can be micronized to achieve such particle diameters.

In such embodiments, the therapeutic substance can make up from about 0.5% to about 30%, or more particularly from about 5% to about 10%, by weight of the total weight of the composition, and the first fluid can make up from about 70% to about 99.5%, or more particularly from about 90% to about 95%, by weight of the total weight of the composition. Selection of a specific weight ratio is dependent on factors such as the material from which the prosthesis to be coated is made and the geometrical structure of the prosthesis as well as the particular first fluid selected and various physical properties of the selected first fluid, such as contact angle, viscosity, and volatility. Selection of a specific weight ratio is also dependent on factors such as the particular therapeutic substance selected, the duration of the release, the cumulative amount of the release, and the release rate that is desired Therapeutic substances or agents suitable for inclusion in the composition include, but are not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S.A., Frankfurt, Germany) methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such suitable antiinflammatories include glucocorticoids such as dexamethasone, methylprednisolone, hydrocortisone and betamethasone and non-steroidal antiinflammatories such as aspirin, indomethacin and ibuprofen. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include actinomycin D as well as derivatives and analogs thereof (manufactured by Sigma-Aldrich, Milwaukee, Wis.; or COSMEGEN® available from Merck & Co., Inc., Whitehouse Station, N.J.), angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suranmin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, genetically engineered epithelial cells, and dexamethasone. While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

In other embodiments, the therapeutic substance is a radioactive isotope or a radiopaque substance. Such substances help to facilitate prosthesis usage in radiotherapeutic procedures. Examples of radioactive isotopes include, but are not limited to, phosphoric acid ($H_3P^{32}O_4$), palladium ($Pd^{103}$), cesium ($Cs^{131}$), and iodine ($I^{125}$). An example of a radiopaque substance is gold.

The first fluid should be a fluid in which the selected therapeutic substance is insoluble or in which the selected therapeutic substance has limited solubility, i.e., less than or equal to 30%, since the therapeutic substance must be primarily suspended as particles in the first fluid rather than dissolved in the first fluid. Exposure of the therapeutic substance to the first fluid is not permitted to adversely alter the substance's composition or characteristic. Accordingly, the particular first fluid is selected for chemical compatibility with the selected therapeutic substance. The particular first fluid selected also depends on the material of which the prosthesis is made. For example, if the prosthesis is made of an absorbable polymer, caution should be exercised in the selection of all fluids since some absorbable polymers of which a prosthesis can be made dissolve in fluids that are otherwise suitable for usage in the present invention. In addition, the first fluid should have a high volatility as well as a low contact angle. Exemplary first fluids include, but are not limited to, deionized water, methanol, ethanol, freon, and acetonitrile.

In some embodiments, the composition additionally includes a polymer, or a combination of polymers, dissolved in the first fluid. The polymeric material is most suitably biocompatible, including polymers that are non-toxic, non-inflammatory, chemically inert, and substantially non-immunogenic in the applied amounts. The polymer is typically either bioabsorbable or biostable. A bioabsorbable polymer breaks down in the body and is not present sufficiently long after implantation to cause an adverse local response. Bioabsorbable polymers are gradually absorbed or eliminated by the body by hydrolysis, metabolic process, bulk, or surface erosion. Examples of bioabsorbable materials include but are not limited to polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates. Biomolecules such as heparin, fibrin, fibrinogen, cellulose, starch, and collagen are typically also suitable. A biostable polymer does not break down in the body, and thus a biostable polymer is present in the body for a substantial amount of time after implantation. Examples of biostable polymers include Parylene®, Parylast®, polyurethane (for example, segmented polyurethanes such as Biospan®), polyethylene, polyethlyene teraphthalate, ethylene vinyl acetate, silicone, polyethylene oxide, and polytetrafluoroethylene (PTFE).

In such embodiments, the polymeric material can make up from about 0.1% to about 30%, or more particularly from about 0.1% to about 10%, by weight of the total weight of the composition, the therapeutic substance can make up from about 0.5% to about 30%, or more particularly from about 0.5% to about 10%, by weight of the total weight of the composition, and the first fluid can make up from about 40% to about 99.4%, or more particularly from about 80% to about 99.4%, by weight of the total weight of the composition. In addition to the factors discussed above, selection of a specific weight ratio is dependent on factors such as the particular polymer, or combination of polymers, selected and the solubility of the selected polymer in the selected first fluid.

In other embodiments, the therapeutic substance is not initially suspended in the first fluid. Rather, the therapeutic substance is first dissolved in a second fluid to form a solution. The second fluid, therefore, must be selected to be a good solvent for the selected therapeutic substance. The above-described first fluid is then slowly added into the therapeutic substance-containing solution. This process precipitates the therapeutic substance from the composition such that a fine colloidal system is formed in situ. The resulting suspension of the therapeutic substance has a very controlled particle size distribution. The size of the suspended particles of therapeutic substance can range from about 0.5 microns in diameter to about 20 microns in diameter, or more particularly from about 0.5 microns in diameter to about 5 microns in diameter.

In such embodiments, the solvent or second fluid can make up from about 50% to about 99%, or more particularly from about 70% to about 99%, by weight of the total weight of the composition, the therapeutic substance can make up from about 0.5% to about 30%, or more particularly from about 0.5% to about 20%, by weight of the total weight of the composition, and the first fluid can make up from about 0.5% to about 20%, or more particularly from about 0.5% to about 10%, by weight of the total weight of the composition. Selection of a specific weight ratio is dependent on factors such as the material from which the prosthesis to be coated is made and the geometrical structure of the prosthesis as well as the particular first and second fluids selected and various physical properties of the selected first and second fluids, such as contact angle, viscosity, and volatility. Selection of a specific weight ratio is also dependent on factors such as the particular therapeutic substance selected, the duration of the release, the cumulative amount of the release, and the release rate that is desired.

In some embodiments in which the therapeutic substance is dissolved in a second fluid prior to being suspended in the first fluid, the composition additionally includes a polymer or a combination of polymers dissolved in the second fluid. Examples of such polymeric materials were listed above, and such examples are equally applicable here. In such embodiments, the polymeric material can make up from about 0.1% to about 30%, or more particularly from about 0.1% to about 10%, by weight of the total weight of the composition, the solvent or second fluid can make up from about 20% to about 89.9%, or more particularly from about 70% to about 89.9%, by weight of the total weight of the composition, the therapeutic substance can make up from about 0.5% to about 30%, or more particularly from about 0.5% to about 10%, by weight of the total weight of the composition, and the first fluid can make up from about 0.5% to about 20%, or more particularly from about 0.5% to about 10%, by weight of the total weight of the composition. Typically, the first fluid should not precipitate the polymer from the second fluid.

In still other embodiments of the composition, a suspension stabilizer is added to minimize flocculation. Flocculation refers to the clumping and/or settling of suspended particles. In this particular instance, flocculation refers to the clumping and/or settling of therapeutic substance particles in the composition. Exemplary deflocculants include, but are not limited to, pluronic, polyvinyl alcohol (PVA), and stearates. Typically, the stabilizer makes up from about 0.1% to about 1% by weight of the total weight of the composition.

Coating the Prosthesis Using the Composition

To form a coating on a surface of the prosthesis, the surface of the prosthesis should be clean and free from contaminants that may be introduced during manufacturing. Other than cleaning, the surface of the prosthesis requires no particular surface treatment to retain the applied coating, although the surface may optionally be subjected to physical treatments, such as, but not limited to, the creation of depots in the surface of the prosthesis, to maximize retention of the coating.

Referring again to FIG. 1, the above-described composition provided in act 101 of method 100 is applied to the prosthesis in act 102. Care should be taken to ensure that the particles of therapeutic substance are suspended in the composition, as opposed to settled at the bottom of the composition, prior to the application of the composition to the prosthesis. The addition of a suspension stabilizer to the composition, as described above, can aid in the prevention of settling of therapeutic substance particles. The composition may also be vortexed for approximately 5–30 seconds just prior to application to the prosthesis to ensure proper suspension of the therapeutic substance.

The above-described composition maybe applied to the surface of a prosthesis in act 102 by any conventional method, such as by spraying the composition onto the prosthesis or immersing the prosthesis in the composition. Variations of spray and immersion techniques are also suitable methods of applying the composition to a surface of a prosthesis. In one such variation, the composition may be applied by spraying or immersing the prosthesis as described above. The composition-coated prosthesis is then centrifuged. The rotation of the prosthesis creates a centrifugal force upon the composition applied to the surface of the prosthesis. This centrifugal force causes excess accumulations of the composition to be more evenly redistributed over the prosthesis and thus provides a more even, uniform coating of the composition on the prosthesis. The rotational speed during centrifugation can be varied. Higher RPM values may provide improved uniformity and a reduction in defects. However, lower RPM values improve the total loading of the composition onto the prosthesis. Increasing the total centrifugation time may also improve the uniformity and reduce defects in the coating of the composition on the prosthesis.

The act 102 of applying the composition to the prosthesis is followed by the removal of the first fluid and any second fluid from the composition on the prosthesis in act 103. The first and second fluids may be removed using techniques such as evaporation at ambient pressure and room temperature in an anhydrous atmosphere for 48 hours, or exposure to mild heat, e.g., 60–65° C., under vacuum conditions. In examples wherein the prosthesis is made of an absorbable polymer, the first and second fluids should be removed relatively quickly to avoid prolonged exposure and thereby ensure the mechanical integrity of the absorbable prosthesis. Upon removal of essentially all of the first fluid and any second fluid, a coating remains on the prosthesis.

In some embodiments, a polymeric coating, without a therapeutic substance, is applied to the prosthesis in act 104 prior to the application of the composition to the prosthesis in act 102. The polymeric layer can serve as a primer to facilitate better adhesion of the composition to the prosthesis and is particularly useful when the composition does not itself contain polymeric material. Examples of suitable polymers were listed above, and such examples are equally applicable here. The polymeric primer can be formed on the prosthesis by any conventional method, such as the immersion or spray techniques described above. By way of example, and not limitation, the polymeric primer can have a thickness of about 0.5 microns to about 2.0 microns. The particular thickness of the layer is dependent on the desired use of the primer and the type of procedure for which the prosthesis is employed. The primer layer should be dried in act 105 prior to the application of the composition onto the primer layer in act 101. Such drying may be accomplished using conventional methods known to one of ordinary skill in the art, such as those described above with reference to the drying of the composition in act 103.

In some embodiments in which a primer is utilized, asperities, or areas of roughness, are created on the polymeric layer in act 106. The asperities enable the primer layer to physically entrap the therapeutic substance-containing composition that is subsequently applied atop the primer layer in act 102. A variety of methods can be used to create the asperities on the primer layer covering the outer surface of the prosthesis.

In one method, a pressurized stream of grit material is directed upon the polymeric primer layer after the primer layer has been dried in act 105. Examples of such processes include bead blasting and sand blasting. Bead blasting refers to the use of pressurized gas to project beads of a relatively uniform diameter at an object at a high velocity. The beads may be made of materials such as, but not limited to, aluminum oxide, silicon oxide, or latex. In sand blasting, the grit projected does not have as uniform a diameter as in bead blasting. Both bead blasting and sand blasting are techniques that are well known to those of ordinary skill in the art. The roughness achieved using a pressurized grit source can be controlled by the size of the grit, e.g., the diameter of the beads, the pressure used, the distance between the grit source and the primer surface, and the length of time the grit is blasted at the primer surface. By way of example and not limitation, the grit can be beads having a diameter of between 10 $\mu$m and 50 $\mu$m. Pressures of 30 PSI (pounds per square inch) to 60 PSI can be used to project the beads from a distance of approximately 3–10 cm from the prosthesis.

In another embodiment, laser etching is used to create asperities on the primer layer after the primer layer has been dried in act 105. Laser lithographic methods are known to those of ordinary skill in the art. A laser is directed onto the primer layer for a predetermined period of time, which depends on the etch rate and the depth of etch desired. A patterned mask that has openings may be applied over the primer layer before the laser is utilized. The laser is then allowed to etch the primer through the openings of the mask. The use of patterned masks with laser etching is known to those of ordinary skill in the art.

In another embodiment, the manner in which the primer is deposited onto the outer surface of the prosthesis in act 104 can create the asperities required in act 106. The primer may be added via physical deposition process, for example, sputtering, which is known to those of ordinary skill in the art. In sputtering, an energy beam, for instance an ion beam, is directed at a target formed of the material which is to be deposited on the substrate. The energy beam dislodges atoms of the target material. The target material atoms are transported to the substrate, which in this instance is the primer-coated stent on which asperities are being formed. Once at the substrate, the atoms form "islands" or small nodules of the deposition material on the substrate.

Conventionally, sputtering is used to form a thin film of the deposition material over the substrate, and sputtering conditions are used such that the "islands" grow, spread, and condense on the substrate to form a thin film. To form the asperities, however, the sputtering conditions are set so that instead of creating a uniform film over the substrate, the "islands" do not grow, spread, and condense, leaving a rough surface. Process conditions in which a lower pressure and shorter deposition time than is typically used for thin film deposition are used to form the asperities in the primer layer. In still another embodiment, a polymeric coating, without a therapeutic substance, is deposited in act 107 on the composition-based coating applied in act 102. The polymeric topcoat can be applied by any conventional method, such as the immersion or spray techniques described above. The polymeric topcoat produces a membrane that reduces the rate of release of the therapeutic substance or substances from the composition-based coating. Examples of suitable polymers were listed above, and such examples are equally applicable here. By way of example, and not limitation, the polymeric topcoat can have a thickness of about 0.25 microns to about 1.5 microns. Typically, the topcoat can have a thickness of about 1 micron. It is understood by one of ordinary skill in the art that the thickness of the polymeric overlayer is based on factors such as the type of procedure for which the prosthesis is employed and the rate of release that is desired. The topcoat should be dried in act 108. Such drying may be accomplished using conventional methods known to one of ordinary skill in the art, such as those described above with reference to the drying of the composition in act 103.

In still another embodiment, both a polymeric primer and a polymeric topcoat are employed via acts 104 and 107, respectively. In this embodiment, a polymeric primer is applied to a clean prosthesis prior to the application of the composition as described above. After the primer layer has been dried, the composition is applied atop the dried primer layer. The polymeric topcoat is applied and dried in acts 107 and 108, respectively, subsequent to the application and drying of the composition in acts 102 and 103, respectively. Such an embodiment facilitates the initial immobilization of the therapeutic substance on the prosthesis followed by the controlled release of the therapeutic substance.

Methods of Use

An implanted stent or graft, having the above-described therapeutic coating, is useful for treating occluded regions of blood vessels caused by thrombosis and/or restenosis, among other possible uses.

Stents may be placed in a wide array of blood vessels, both arteries and veins. Briefly, an angiogram is first performed to determine the appropriate positioning for stent therapy. Angiograms are typically accomplished by using a catheter to inject a radiopaque contrasting agent into an artery or vein as an X-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein and advanced into the appropriate blood vessel by steering the catheter through the vascular system under fluoroscopic guidance. A stent having the above described covering may then be expanded at the desired area of treatment. A post-insertion angiogram may also be utilized to confirm appropriate positioning.

Vascular grafts may be used to replace, bypass, or reinforce diseased or damaged sections of a vein or artery. The general procedure for implantation includes the step of pre-clotting, wherein the graft is immersed in the blood of the patient and allowed to stand for a period of time sufficient for clotting to ensue. After pre-clotting, hemorrhaging is less likely to occur when the graft is implanted, and thus the growth of tissue is not impeded. Grafts may be placed either through invasive surgery or non-invasively through percutaneous endoluminal transport. Percutaneous delivery of a graft avoids the complications and risks of surgery. The graft may be attached to the vessel at each end of the diseased region, thus bypassing the diseased region. Alternatively, the diseased region may be removed and replaced by the graft.

EXAMPLES

Exemplary embodiments of the invention are illustrated below. These examples are being given by way of illustration only and not by way of limitation. The parameters given, including percentages of fluids, therapeutic substance, polymers, temperature, duration of time, and other data, are exemplary, not limiting.

Example 1

The following is an exemplary method in which the composition includes a therapeutic substance and a first fluid. A polymeric primer layer and a polymeric topcoat are also employed.

Multi-Link Duet™ stents (available from Guidant Corporation) are cleaned by placement in an ultrasonic bath of isopropyl alcohol solution for 10 minutes. The stents are air-dried. A primer coating of ethylene vinyl alcohol copolymer (EVOH) is made with 1 gram of EVOH and 5 grams of dimethyl sulfoxide (DMSO), yielding an EVOH:DMSO ratio of 1:5. The EVOH is dissolved by placing the vial of EVOH:DMSO solution on a roller bottle apparatus in an oven at 60° C. for 6 hours. The EVOH:DMSO solution is sprayed onto the cleaned Multi-Link Duet™ stents. The primer-coated stents are placed in an oven at 60° C. for 4 hours.

A 5% suspension of actinomycin D is made by adding 0.05 gram of actinomycin D to 1 gram of methanol. The primer-coated stents are dipped into the suspension for 5 seconds. The actinomycin D-coated stents are then air-dried for 15 minutes.

An EVOH topcoating, which is prepared in the same manner as the primer coating above, is sprayed onto the actinomycin D-coated stents. The coated stents are placed in a convection oven at 50° C. for 4 hours. The average amount of actinomycin D retained on the stents is about 39 micrograms.

Example 2

The following is another exemplary method in which the composition includes a therapeutic substance and a first fluid. A polymeric primer layer and a polymeric topcoat are also employed.

Multi-Link Duet™ stents are cleaned by placement in an ultrasonic bath of isopropyl alcohol solution for 10 minutes.

The stents are air-dried. A primer coating of EVOH is made with 1 gram of EVOH and 7 grams of DMSO, yielding an EVOH:DMSO ratio of 1:7. The EVOH is dissolved by placing the vial of EVOH:DMSO solution on a roller bottle apparatus in an oven at 60° C. for 6 hours. The EVOH:DMSO solution is applied to the cleaned Multi-Link Duet™ stents by a modified dip method. The primer-coated stents are placed in an oven at 60° C. for 4 hours.

A 5% suspension of actinomycin D is made by adding 0.05 gram of actinomycin D to 1 gram of methanol. The primer-coated stents are dipped into the suspension for 5 seconds. The actinomycin D-coated stents are then air-dried for 15 minutes.

An EVOH topcoating, which is prepared in the same manner as the primer coating above, is sprayed onto the actinomycin D-coated stents. The coated stents are placed in a convection oven at 50° C. for 4 hours. The average amount of actinomycin D retained on the stents is about 15 micrograms.

Example 3

The following is an exemplary method in which the composition includes a therapeutic substance, a first fluid, a polymer, and a suspension stabilizer.

A Multi-Link Duet™ stent is cleaned by placement in an ultrasonic bath of isopropyl alcohol solution for 10 minutes. The stent is air-dried. An EVOH:DMSO solution is made with 1 gram of EVOH and 4 grams of DMSO, making a solution having a EVOH:DMSO ratio of 1:4. Actinomycin D is added to the EVOH:DMSO solution to form a suspension. Actinomycin D constitutes 10% by weight of the total weight of the suspension. Pluronic, a suspension stabilizer, is added to the suspension to slow the flocculation rate of the suspended actinomycin D particles. The suspension stabilizer constitutes 0.5% by weight of the total weight of the suspension. The suspension is vortexed for 10 seconds. The viscosity of the EVOH:DMSO solution is adequate to slow the flocculation rate of the suspended actinomycin D particles for approximately 30 minutes. The cleaned Multi-Link Duet™ stent is attached to mandrel wires and dipped into the suspension. The coated stent is then placed in a vacuum oven at 60° C. for 24 hours. It is predicted that the coating will remain intact on the stent.

Example 4

The following is an exemplary method in which the composition includes a therapeutic substance, a first fluid, a second fluid, and a polymer.

A Multi-Link Duet™ stent is cleaned by placement in an ultrasonic bath of isopropyl alcohol solution for 10 minutes. The stent is air-dried. An actinomycin D:tetrahydrofuran (THF) solution is made with 0.32 gram of actinomycin D and 4 grams of THF, making a solution having an actinomycin D:tetrahydrofuran (THF) ratio of 2:23. An EVOH:DMSO solution is made with 1 gram of EVOH and 4 grams of DMSO, making a solution having a EVOH:DMSO ratio of 1:4. The EVOH:DMSO solution is gradually added into the actinomycin D:THF solution. This process precipitates the actinomycin D from the actinomycin:THF solution. Actinomycin D constitutes 3.4% by weight of the total weight of the suspension. The suspension is vortexed for 10 seconds. The viscosity of the EVOH:DMSO:THF solution is adequate to slow the flocculation rate of the suspended actinomycin D particles. The cleaned Multi-Link Duet™ stent is attached to mandrel wires and dipped into the suspension. The coated stent is then placed in a vacuum oven at 60° C. for 24 hours. It is predicted that the coating will remain intact on the stent.

Example 5

The following is an exemplary method in which the composition includes a therapeutic substance, a first fluid, and a suspension stabilizer. A polymeric primer layer is also employed.

A synthetic graft made from polytetrafluoroethylene (PTFE) is cleaned by placement in an ultrasonic bath of isopropyl alcohol solution for 10 minutes. The graft is air-dried. An EVOH solution is made with 1 gram of EVOH and 7 grams of DMSO, making an EVOH:DMSO ratio of 1:7. The mixture is placed in a warm water shaker bath at 60° C. for 24 hours. The solution is cooled and vortexed. The cleaned graft is dipped in the EVOH:DMSO solution. The coated graft is then placed in a oven at 60° C., under vacuum condition, and for 24 hours. The coating will provide a primer layer to facilitate adhesion of the following actinomycin D layer.

A suspension of actinomycin D in DMSO:THF:EVAL is made with 0.32 gram of actinomycin D and 9 grams of DMSO:TBF:EVAL, such that actinomycin D constitutes 3.4% by weight of the total weight of the suspension. The suspension is vortexed for 10 seconds. Pluronic, a suspension stabilizer, is added to the suspension to slow the flocculation rate of the suspended actinomycin D particles. The suspension stabilizer constitutes 0.5% by weight of the total weight of the suspension. The primer-coated graft is attached to mandrel wires and dipped into the suspension. The coated graft is then placed in a vacuum oven at 60° C. for 24 hours. It is predicted that the coatings will remain intact on the graft.

Example 6

The following is an exemplary method in which the composition includes a therapeutic substance and a first fluid. A polymeric topcoat is also employed.

A stent having cavities formed in the surface thereof is cleaned by placement in an ultrasonic bath of isopropyl alcohol solution for 10 minutes. The stent is air-dried. Cisplatin is micronized using a mortar and pestle assembly to yield particles ranging in size from 1–2 microns. A suspension of cisplatin in dimethyl formamide (DMF) is made such that cisplatin constitutes 5% by weight of the total weight of the suspension. The suspension is vortexed vigorously for 10 seconds to prevent flocculation. The cleaned stent is attached to mandrel wires and dipped into the suspension. The excess suspension is removed by lightly touching a highly porous, lint-free cloth to the stent for 30 seconds.

The cisplatin-coated stent is dipped into a 1:4 EVOH:DMSO solution, free from cisplatin. The stent is placed in the oven to dry as previously described. The top coating will provide a barrier layer for controlling the release of cisplatin from the cisplatin layer. It is predicted that the coatings will remain intact on the stent.

Example 7

The following is an exemplary method in which the composition includes a therapeutic substance and a first fluid. A polymeric primer layer and a polymeric topcoat are also employed.

A Multi-Link Duet™ stent is cleaned by placement in an ultrasonic bath of isopropyl alcohol solution for 10 minutes.

The stent is air-dried. An EVOH:DMSO solution is made with 1 gram of EVOH and 7 grams of DMSO, making an EVOH:DMSO ratio of 1:7. The mixture is placed in a warm water shaker bath at 60° C. for 24 hours. The solution is cooled and vortexed. The cleaned Multi-Link Duet™ stent is dipped in the EVOH:DMSO solution. The EVOH-coated stent is placed in a oven at 60° C., under vacuum condition, and for 24 hours. The coating will provide a primer layer for the following cisplatin layer.

Cisplatin is micronized using a mortar and pestle assembly to yield particles ranging in size from 1–2 microns. A suspension of cisplatin in dimethyl formamide (DMF) is made such that cisplatin constitutes 5% by weight of the total weight of the suspension. The suspension is vortexed vigorously for 10 seconds to prevent flocculation. The primer-coated stent is attached to mandrel wires and dipped into the suspension. The excess suspension is removed by lightly touching a highly porous, lint-free cloth to the stent for 30 seconds.

The cisplatin-coated stent is dipped into a 1:4 EVOH:DMSO solution, free from cisplatin. The stent is placed in the oven to dry as previously described. The top coating will provide a barrier layer for controlling the release of cisplatin from the cisplatin layer. It is predicted that the coatings will remain intact on the stent.

Example 8

The following is an another exemplary method in which the composition includes a therapeutic substance and a first fluid. A polymeric primer layer and a polymeric topcoat are also employed.

A synthetic graft made from expanded polytetrafluoroethylene (ePTFE) is cleaned by placement in an ultrasonic bath of isopropyl alcohol solution for 10 minutes. The graft is air-dried. An EVOH:DMSO solution is made with 1 gram of EVOH and 7 grams of DMSO, making an EVOH:DMSO ratio of 1:7. The mixture is placed in a warm water shaker bath at 60° C. for 24 hours. The solution is cooled and vortexed. The cleaned graft is dipped in the EVOH:DMSO solution. The EVOH-coated graft is placed in a oven at 60° C., under vacuum condition, and for 24 hours. The coating will provide a primer layer for the following cisplatin layer.

Cisplatin is micronized using a mortar and pestle assembly to yield particles ranging in size from 1–2 microns. A suspension of cisplatin in methanol is made such that cisplatin constitutes 5% by weight of the total weight of the suspension. The suspension is vortexed vigorously to prevent flocculation. The primer-coated graft is dipped into the suspension. The excess suspension is removed by lightly touching a highly porous, lint-free cloth to the stent for 30 seconds.

The cisplatin-coated graft is dipped into a 1:4 EVOH:DMSO solution, free from cisplatin. The graft is placed in the oven to dry as previously described. The top coating will provide a barrier layer for controlling the release of cisplatin from the cisplatin layer. It is predicted that the coatings will remain intact on the graft.

While particular embodiments, applications, and examples of the present invention have been shown and described, it will be apparent to those of ordinary skill in the art that changes and modifications can be made without departing from this invention in its broader aspects. Therefore, the appended claims are to encompass within their scope all such changes and modifications as fall within the true spirit and scope of this invention.

What is claimed is:

1. A method of producing a composition which can be used to coat an implantable medical device comprising:
   combining a therapeutic substance;
   a fluid; and
   a suspension stabilizer wherein the suspension stabilizer reduces the flocculation of the therapeutic substance within the composition,
   wherein
   the therapeutic substance has a limited solubility in the fluid such that
   the fluid is not capable of significantly dissolving the therapeutic substance,
   wherein
   a majority amount of the therapeutic substance is suspended in
   particle or
   solid form
   in the fluid and
   is not dissolved in the fluid.

2. The method of claim 1, wherein the device is selected from a group of balloon-expandable stents, self-expandable stents, and grafts.

3. The method of claim 1, wherein greater than 50% and less than or equal to 100% of the therapeutic substance is suspended as particles or is in solid form in the composition.

4. The method of claim 1, wherein about 70% to about 100% of the therapeutic substance is suspended as particles or is in solid form in the composition.

5. The method of claim 1, wherein the particles of the therapeutic substance have diameters ranging from about 0.5 microns to about 20 microns.

6. The method of claim 1, wherein the fluid is a combination of at least two fluids.

7. The method of claim 1, wherein the fluid is a combination of at least two fluids, wherein at least one of the fluids is a solvent for the therapeutic substance and at least one of the fluids is a non-solvent for the therapeutic substance.

8. The method of claim 1, additionally comprising adding a polymeric material to the composition.

9. The method of claim 8, wherein the fluid is capable of dissolving the polymeric material.

10. A method comprising:
    combining a therapeutic substance, a fluid, and a suspension stabilizer, wherein the suspension stabilizer reduces the flocculation of the therapeutic substance within the combination; and
    depositing the combination onto a medical device,
    wherein the therapeutic substance has a limited solubility in the fluid
    such that the fluid is not capable of significantly dissolving the therapeutic substance,
    wherein a majority amount of the therapeutic substance is
    suspended in
    particle or
    solid form
    in the fluid and
    is not dissolved in the fluid.

11. The method of claim 10 wherein the device is a balloon-expandable stent, self-expandable stent, or graft.

12. The method of claim 10 wherein 50%–100% of the therapeutic substance is suspended as particles or is in solid form in the combination.

13. The method of claim 10 wherein about 70% to about 100% of the therapeutic substance is suspended as particles or is in solid form in the combination.

14. The method of claim 10 wherein the particles of the therapeutic substance have diameters ranging from about 0.5 microns to about 20 microns.

15. The method of claim 10 wherein the fluid is a combination of at least two fluids.

16. The method of claim 10 wherein the fluid is a combination of at least two fluids, wherein at least one of the fluids is a solvent for the therapeutic substance and at least one of the fluids is a non-solvent for the therapeutic substance.

17. The method of claim 10 additionally comprising adding a polymeric material to the combination.

18. The method of claim 17 wherein the fluid is capable of dissolving the polymeric material.

19. A method comprising:
   combining a therapeutic substance;
   a fluid; and
   a suspension stabilizer that reduces the flocculation of the therapeutic substance within the combination; and
   depositing the combination onto an implantable medical device,
   wherein the therapeutic substance has a limited solubility in the fluid
      such that the fluid is not capable of significantly dissolving the therapeutic substance,
   wherein a majority amount of the therapeutic substance is suspended in
      particle or
      solid form
      in the fluid and
      is not dissolved in the fluid and
   wherein
      the implantable medical device can
      retain the therapeutic substance
      for the local delivery of the substance
      upon removal of the fluid.

20. The method of claim 19 wherein the device is a balloon-expandable stent, self-expandable stent, or graft.

21. The method of claim 19 wherein 50%–100% of the therapeutic substance is suspended as particles or is in solid form in the combination.

22. The method of claim 19 wherein about 70% to about 100% of the therapeutic substance is suspended as particles or is in solid form in the combination.

23. The method of claim 19 wherein the particles of the therapeutic substance have diameters ranging from about 0.5 microns to about 20 microns.

24. The method of claim 19 wherein the fluid is a combination of at least two fluids.

25. The method of claim 19 wherein the fluid is a combination of at least two fluids, wherein at least one of the fluids is a solvent for the therapeutic substance and at least one of the fluids is a non-solvent for the therapeutic substance.

26. The method of claim 19 additionally comprising adding a polymeric material to the combination.

27. The method of claim 26 wherein the fluid is capable of dissolving the polymeric material.

28. A method comprising:
   forming a combination consisting essentially of a therapeutic substance, a fluid, and a suspension stabilizer, wherein the suspension stabilizer reduces the flocculation of the therapeutic substance within the combination; and
   depositing the combination onto a medical device,
   wherein the therapeutic substance has a limited solubility in the fluid
      such that the fluid is not capable of significantly dissolving the therapeutic substance,
   wherein a majority amount of the therapeutic substance is suspended in
      particle or
      solid form
      in the fluid and
      is not dissolved in the fluid.

29. The method of claim 28 wherein the device is a balloon-expandable stent, self-expandable stent, or graft.

30. The method of claim 28 wherein 50%–100% of the therapeutic substance is suspended as particles or is in solid form in the combination.

31. The method of claim 28 wherein about 70% to about 100% of the therapeutic substance is suspended as particles or is in solid form in the combination.

32. The method of claim 28 wherein the particles of the therapeutic substance have diameters ranging from about 0.5 microns to about 20 microns.

33. The method of claim 28 wherein the fluid is a combination of at least two fluids.

34. The method of claim 28 wherein the fluid is a combination of at least two fluids, wherein at least one of the fluids is a solvent for the therapeutic substance and at least one of the fluids is a non-solvent for the therapeutic substance.

35. The method of claim 28 additionally comprising adding a polymeric material to the combination before the deposition step.

36. The method of claim 35 wherein the fluid is capable of dissolving the polymeric material.

* * * * *